US009839430B2

(12) United States Patent
Willems et al.

(10) Patent No.: US 9,839,430 B2
(45) Date of Patent: Dec. 12, 2017

(54) DEVICE FOR CLOSING OPENINGS OR CAVITIES IN BLOOD VESSELS

(75) Inventors: Frank Willems, Moers (DE); Christoph Classen, Houschian (DE); Andreas Henseler, Simmerath (DE); Wolfgang Witt, Moers (DE)

(73) Assignee: Occlutech Holding AG, Schaffhausen (CH)

( * ) Notice: Subject to any disclaimer, the term of this patent is extended or adjusted under 35 U.S.C. 154(b) by 0 days.

(21) Appl. No.: 13/821,089

(22) PCT Filed: Sep. 6, 2011

(86) PCT No.: PCT/EP2011/065367
§ 371 (c)(1),
(2), (4) Date: Oct. 18, 2013

(87) PCT Pub. No.: WO2012/032030
PCT Pub. Date: Mar. 15, 2012

(65) Prior Publication Data
US 2014/0039543 A1 Feb. 6, 2014

(30) Foreign Application Priority Data

Sep. 6, 2010 (EP) .................... 10175452

(51) Int. Cl.
*A61B 17/08* (2006.01)
*A61B 17/12* (2006.01)
*A61B 17/00* (2006.01)

(52) U.S. Cl.
CPC .... *A61B 17/12109* (2013.01); *A61B 17/0057* (2013.01); *A61B 2017/00575* (2013.01);
(Continued)

(58) Field of Classification Search
CPC ...... A61B 2017/10; A61B 2017/00623; A61B 2017/00672; A61B 2017/00646;
(Continued)

(56) References Cited

U.S. PATENT DOCUMENTS 6,375,668 B1 * 4/2002 Gifford ............ A61B 17/12022
606/200
2005/0113868 A1 5/2005 Devellian et al.
(Continued)

FOREIGN PATENT DOCUMENTS

EP 1046375 A1 10/2000
WO 2007092902 A2 8/2007
(Continued)

OTHER PUBLICATIONS

International Search Report for corresponding Patent Application No. PCT/EP2011/065367 dated Nov. 24, 2011.
(Continued)

*Primary Examiner* — Jonathan Miles
*Assistant Examiner* — Majid Jamialahmadi
(74) *Attorney, Agent, or Firm* — Inskeep IP Group, Inc.

(57) ABSTRACT

The device for closing openings or cavities in blood vessels, e.g. in veins or in the heart, said device comprises a closing body comprising an outer side having a partial region arranged for blood flow therealong at least in a part of said partial region thereof when said closing body is in its state of use for closing said opening or cavity. Furthermore, the device comprises at least one layer (16) of biostable non-woven fiber material, which at least within a partial surface of said partial region of said outer side of the closing body is at least partially in abutment on the closing body.

19 Claims, 1 Drawing Sheet

Figure 1:
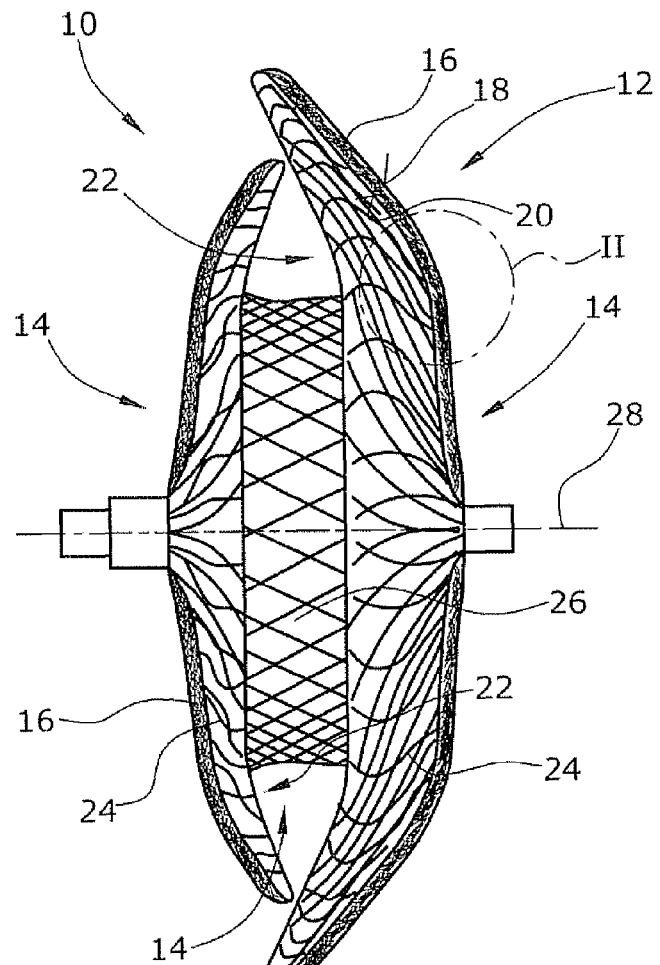

(52) U.S. Cl.
CPC ............... *A61B 2017/00597* (2013.01); *A61B 2017/00606* (2013.01); *A61B 2017/00867* (2013.01)

(58) Field of Classification Search
CPC .......... A61B 2017/00637; A61B 17/08; A61B 17/0057; A61B 2017/00575; A61B 17/1215; A61B 2017/00597; A61B 17/12022; A61B 17/12109; A61B 2017/00606
USPC ....... 606/158, 135, 213, 200, 215, 151, 153, 606/139; 623/23.72, 23.73, 23.74, 623/1.1–1.22; 128/831, 834, 842; 424/426, 423; 442/340, 350, 351, 414; 428/311.11, 311.51, 315.5, 903
See application file for complete search history.

(56) References Cited

U.S. PATENT DOCUMENTS

| | | | |
|---|---|---|---|
| 2007/0066993 A1 | 3/2007 | Kreidler | |
| 2007/0082021 A1* | 4/2007 | Bates | 424/423 |
| 2008/0109072 A1* | 5/2008 | Girton | 623/1.49 |
| 2008/0110342 A1 | 5/2008 | Ensor et al. | |
| 2009/0062844 A1* | 3/2009 | Tekulve et al. | 606/213 |
| 2009/0157172 A1* | 6/2009 | Kokate et al. | 623/1.43 |
| 2009/0182372 A1 | 7/2009 | Kladakis et al. | |
| 2010/0030246 A1* | 2/2010 | Pavcnik et al. | 606/157 |
| 2011/0082495 A1* | 4/2011 | Ruiz | A61B 17/0057 606/213 |
| 2011/0152993 A1* | 6/2011 | Marchand | A61B 17/12022 623/1.2 |
| 2011/0202088 A1* | 8/2011 | Eckhouse et al. | 606/200 |

FOREIGN PATENT DOCUMENTS

| | | | | |
|---|---|---|---|---|
| WO | 2009029261 A1 | 3/2009 | | |
| WO | WO 2010/046897 | * | 4/2010 | 606/200 |

OTHER PUBLICATIONS

Written Opinion for corresponding Patent Application No. PCT/EP2011/065367 dated Nov. 30, 2011.

* cited by examiner

DEVICE FOR CLOSING OPENINGS OR CAVITIES IN BLOOD VESSELS

This application is a national phase of International Application No. PCT/EP2011/065367 filed Sep. 6, 2011 and published in the English language.

The present invention relates to a device for closing openings or cavities in blood vessels, e.g. in veins or in the heart.

Devices for closing openings or cavities in blood vessels are also known as occluders. Occluders can have different designs and basically comprise a compressible construction of metallic fibers which are self-expandable. Accordingly, occluders can be placed in an opening or cavity by guiding the occluder through the lumen of a catheter.

The principles of certain kinds of devices for closing openings or cavities in blood vessels and for occluders as well as the medical indications for these devices are disclosed in WO-A-2007/124862, WO-A-99/12478, US-A-2007/0043391, U.S. Pat. No. 5,725,552, DE-A-10 2009 036 818, DE-A-10 2009 036 817, DE-A-10 2008 015 781, DE-A-10 2006 056 283, DE-A-10 2005 053 958, and DE-A-10 2005 053 957.

Implanting an occluder in the human body is not without risk. The risks which exist are similar to the risks given when implanting vascular prostheses or vascular supports such as "stents" serving for holding open e.g. a blood vessel. Some of these problems will be shortly outlined hereinbelow.

In particular, vascular supports are used for treatment of aneurysms in vessels. In this case, use is made of special vascular supports whose wall is formed by a closed material, normally, a polymer of little elasticity. These vascular supports have to be implanted with the aid of a complex applicator in order to allow them to be converted, within the vessel, from a folded state to an expanded state and to be placed in position. This process entails the risk that folds may be generated in cases where it had not been possible to accomplish an optimal adaptation of the vascular support diameter to the vessel diameter.

In addition to that, blood irritation may be induced by the material used for the covering. As a result, thrombus formation or hyperplasia in the area of the implanted device may occur which leads to undesired complications and risks for the patient.

It is an object of the present invention to provide a device for closing openings or cavities in blood vessels wherein the risk of the above mentioned complications during and after implantation is reduced.

According to the present invention, the above object is achieved by a device for closing openings or cavities in blood vessels, e.g. in veins or in the heart, said device comprising a closing body comprising an outer side having a partial region arranged for blood flow therealong at least in a part of said partial region thereof when said closing body is in its state of use for closing said opening or cavity, and at least one layer of biostable nonwoven fiber material, which at least within a partial surface of said partial region of said outer side of the closing body is at least partially in abutment on the closing body.

The invention further proposes a method for producing said device wherein, according to said method, there is first provided said closing body and, for positioning of said layer of biostable nonwoven fiber material, the closing body is sprayed with fibers by use of a spraying device while the closing body and the spraying device are moved relative to each other, and wherein, in dependence on the desired thickness of said layer of biostable nonwoven fiber material, a plurality of layers of fibers are sprayed on.

In essence, the invention resides in that the closing body for closing an opening or cavity in a blood vessel will be provided with a biostable nonwoven fiber material comprising interconnected and, particularly, fine-fibrillated fibers made e.g. of polyurethane. In this arrangement, the biostable nonwoven fiber material is at least partially in abutment on the outer side and/or on the inner side of the closing body of the device wherein the nonwoven fiber material at least partially covers the outer side and/or the inner side of the closing body. The nonwoven fiber material can comprise random-fibers or groups of fibers having different orientations with the fibers of each group having substantially the same orientation.

Said nonwoven fiber material, which is biostable, i.e. under physiological conditions is substantially not absorbable, preferably comprises a fine-fibrillated nonwoven material whose fibers are connected to each other. Particularly, this nonwoven fiber material can have such a porosity that the liquid components of the blood or of the substances taken up by the blood vessel will be substantially allowed to pass while, however, the cellular components of the blood or of the substances taken up by the blood vessel and of the vessel wall will be substantially retained. This feature advantageously allows for a complete exchange of liquids and chemical elements, particularly of nutrients, metabolites and other physiological substances between the inner fluid and the vessel wall. By the nonwoven fiber material of the invention, the closing body can be stretched in an isotropic manner, which is of advantage for a multi-dimensional closing function that is effective in a plurality of spatial directions.

According to a further advantageous embodiment of the invention, it is provided that the nonwoven fiber material layer in the area of the inner surface has a porosity which is smaller than the porosity on the outer surface of the nonwoven fiber material layer. When viewed in the thickness direction of the nonwoven fiber material layer, the porosity of the nonwoven fiber material can vary in a continuous, quasi-continuous or step-wise manner.

According to a further advantageous embodiment of the invention, the biostable nonwoven fiber material, on its inner surface which comes into contact with the substances taken up by the blood vessel, is capable of rendering possible, or facilitating, the adherence and colonization of blood cells, stem cells, progenitor cells or blood-vessel wall cells or, more generally, of cells of the substances taken up by the blood vessels. This is achieved particularly by corresponding selection of the porosity of the nonwoven fiber material on the surface thereof which comes into contact with the biological tissue, and of the porosity at that site of the nonwoven fiber material layer which is in connection with the substance taken up by the blood vessel. The porosity at said above described surface of the nonwoven fiber material is selected to the effect that the connective tissue proliferating from the blood vessel cannot penetrate the nonwoven fiber material layer. Thereby, the risk that the blood vessel might become clogged or overgrown later on is minimized.

According to a further advantageous embodiment of the invention, the nonwoven fiber material layer comprises an outer surface and an inner structure which renders possible or facilitates the integration of the connective tissue.

Finally, it is advantageous if the nonwoven fiber material layer is tightly connected with the closing body of the device. This is suitable primarily because, in this manner, the position of the nonwoven fiber material layer relative to the closing body will not be changed during the implanting of the closing body as well as subsequently, i.e. in situ.

According to a further advantageous embodiment of the invention, it is provided that the elasticity and the porosity of the nonwoven fiber material are adjusted in such a manner that the desired pore size for promoting a well-aimed cell migration will be obtained only after a possible intended dilatation of the closing body. The inventive biostable nonwoven fiber material will expand corresponding to the dilatation of the closing body, as far as such a preferably permanently expandable closing body is used in the inventive device. In such a device, it is of advantage if, in the dilated state, the pore size of the nonwoven fiber material has the desired value or is in the desired range of values. On the basis of the degree of dilatation and the properties of the nonwoven fiber material used, it can be determined, by backward calculation, which pore size the nonwoven fiber material should have in the not-yet-dilated state of the closing body in order to accomplish a desired pore size or range of pore sizes in the nonwoven fiber material and respectively in its surfaces. In any case, the elasticity of the nonwoven fiber material has to be provided to the effect that the dilated closing body cannot be squeezed together again by the widened nonwoven fiber material.

The inventive arrangement of a layer of biostable nonwoven fiber material with at least partial abutment on the closing body of a device surprisingly leads to a lower postoperative complication rate after implantation of a closing body for the purpose of closing openings and/or cavities in blood vessels. Both the risk of plaque rupture and the consequences of such a plaque rupture due to the placement of a closing body are considerably reduced by using a nonwoven fiber material layer on the closing body. In this manner, an occlusion of peripheral vessels is prevented.

According to a further advantageous embodiment of the invention, it is provided that the biostable nonwoven fiber material completely covers the outer side and/or the inner side of the closing body.

A further functional advantage of the invention can be seen in the feature that the nonwoven material layer does not represent a compactly closed structure but instead consists of a three-dimensional, microporous, fine-fibrillated fiber structure. Thereby, the physiology of the vessel wall is not restricted as much as when using dense, closed materials. Thus, this material structure allows for an exchange of substances from and to the vessel wall and also offers the possibility of a selective adhesion, migration and proliferation of cells. The result is the generation of an endothelium-like layer which can be formed toward the blood.

By the differentiated configuration of the nonwoven fibrous structure, a well-aimed colonization of cells is achieved. Thereby, the closing body will become completely fixed in position by integrative healing, so that the inventive product can be conceived of as a catalyst for the reestablishment of physiological conditions on the vessel wall.

The invention described herein is applicable in biological vessel systems, particularly in coronary vessels, peripheral vessels (arterial and venous applications) and neurovascular vessels. Apart from these types of vessels, the opening or cavity which can be closed by the inventive closing body also may include lymph vessels, renal ducts, urethrae, the esophagus, nerve cords or uterine tubes. Also openings and/or cavities in the veins or in the heart such as PFO (patent foraman ovale), ASD (Atrial Septal Defects), VSD (Ventricular Septal Defects), and LAA (Left Aterial Apendage) or other blood vessel openings such as PDA (Patent Ductus Arteriosus) can be closed using a device according to the invention.

In another application, the closing body as provided according to the invention can be used for therapy of vessel aneurysms of any type (fusiform, sacriform, pedunculated and non-pedunculated aneurysms). By the presence of the microporous nonwoven fibrous structure, there will first occur a stasis and a thrombosis formation in the aneurysmal sac. Subsequent wound healing processes with absorption of the thrombus and a replacement of connective tissue will allow the aneurysm to heal. Also here, the later formation of a functional endothelium layer on the inner side of the implant will very quickly lead to laminar flow conditions in the area of the aneurysm. This physiological replacement for closure of the aneurysmal sac is safer and requires distinctly less time for the surgical intervention than is possible e.g. through the conservative method by filling with coils. By implanting the closing body the aneurysmal sac is closed so that blood flows through the lumen of the closing body, thereby preventing further ingress of blood into the aneurismal sac. Moreover, this closure of the aneurysmal sac prevents thrombogenesis in the blood vessel.

According to a still further embodiment, the invention is suited for use also in the non-vascular region. Also in this application, the promotion of a physiological cell proliferation by the fine-fibrillated nonwoven fiber material for thus forming a natural vessel-wall layer is of eminent advantage.

In case of an application for tumor diseases, the tumor tissue can hardly grow through the areal enclosure into the lumen.

The biostable nonwoven fiber material of the device of the invention is suitably formed from an elastomer, preferably form a thermoplastic elastomer. With preference, the nonwoven fibrous structure is made of polyurethane, particularly linear polyurethane. With particular advantage, the polyurethane is an aliphatic polyurethane, preferably formed of macromolecular and/or low-molecular aliphatic dials as well as aliphatic diisocyanates. According to the invention, it is especially preferred that said macromolecular dials are polycarbanates, particularly 1,6-hexanediol polycarbonate. Said low-molecular dials preferably are 2,2,4-trimethylhexanediol, 2,4,4-trimethylhexanediol and/or 1,4-butanediol. Preferably, said aliphatic diisocyanates are 4,4'-dicyclohexylmethane diisocyanate or 1,4-cyclohexyl diisocyanate. According to the invention, it can further be preferred that said aliphatic polyurethane is formed of different dials and/or diisocyanates, wherein preference is given to the dials and diisocyanates described in this paragraph. Concerning further details and features of polyurethanes, reference is made to DE-A-36 43 465, DE-A-33 18 730, DE-A-41 07 284 and to the polymer report "Biocompatible Polyurethanes for Medical Techniques" of the research institute of Enka AG in Obernburg, wherein the disclosure of each of said documents is herewith, by way of reference, incorporated to its full extent into the present description.

According to the invention, the nonwoven fiber material layer comprises fibers having a diameter from 0.1 µm to 100 µm, preferably from 0.2 µm to 20 µm and more preferably from 0.3 µm to 1 µm.

According to the arrangement of the invention, the nonwoven fiber material layer has a bottom side which is in abutment on the outer side of the closing body, and a top side facing away from the outer side of the closing body. Further, the nonwoven fiber material layer comprises, on its top side, pores of a size different from that of the pores on its bottom side. According to the invention, the pores on the bottom side of the nonwoven fiber material layer are smaller than the pores on the top side of the nonwoven fiber material layer. The ratio between the pore size on bottom side and the pore size on top side is 1:50, preferably 2:10 and more preferably 4:8.

The nonwoven fiber material layer has a thickness from 10 μm to 3000 μm.

According to a preferred embodiment of the invention, the closing body is expandable, particularly in a permanent manner, with the nonwoven fiber material layer being stretched at the same time, wherein, prior to the expansion, the thickness of the nonwoven fiber material layer is from 100 μm to 3000 μm, preferably from 150 μm to 2800 μm and more preferably between 200 μm and 2000 μm.

According to a further preferred embodiment of the invention, the closing body is expandable, particularly in a permanent manner, with the nonwoven fiber material layer being stretched at the same time, wherein, after the expansion, the thickness of the nonwoven fiber material layer is from 10 μm to 2500 μm, preferably from 20 μm to 2000 μm and more preferably between 80 μm and 1000 μm.

According to the invention, the closing body comprises a further layer of biostable nonwoven fiber material, wherein the inner side and the outer side of the closing body each comprise respectively one nonwoven fiber material layer which is arranged at least partially in abutment on the respective side and which covers at least partially the inner and/or outer side.

According to the invention, the closing body is porous and particularly has a reticular structure which typically is hollow. Moreover, the closing body typically is self-expandable or is expandable with the aid of a tool. Finally, the closing body may comprise a mesh fabric of fibers, particularly metallic fibers preferably made of metallic memory shape alloy or Nitinol (NiTi alloy).

In the inventive method for producing the device there can be performed e.g. the process steps described in WO-A-2011/054932. According to these methods, whose features are herewith, by way of reference to the respective documents, incorporated into the present application, the nonwoven fiber material is sprayed in the form of microfibers onto a rotating shaped member. According to the invention, said shaped member comprises the closing body of the device.

Preferably, in said method, there is first provided the closing body and, with the aid of a spraying device, the closing body is sprayed with fibers for thus applying the layer of biostable nonwoven fiber material. In the process, the closing body and the spraying device are moved relative to each other. In dependence on the desired thickness of the layer of biostable nonwoven fiber material and/or the desired porosity, a plurality of fiber layers will be spray-deposited, optionally with different areal densities.

Figure 2:
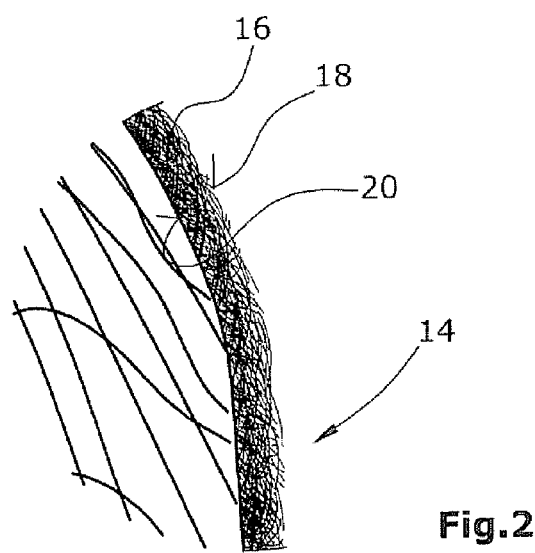

A full and enabling disclosure of the present invention, including the best mode thereof, enabling one of ordinary skill in the art to carry out the invention, is set forth in greater detail in the following description, including reference to the accompanying drawing in which FIG. 1 is a lateral view of an embodiment of an occluder (as an example of a closing body which in this embodiment is an ASD occluder), and FIG. 2 is an enlarged view of the detail II in FIG. 1.

FIG. 1 shows, in lateral view, an ASD occluder 10 comprising a reticular or net-shaped or braided closing body 12 whose outer side 14 at least in part is provided with a layer 16 of biostable nonwoven fiber material. Said nonwoven fiber material layer 16 comprises e.g. random fibers made of microfibers. The nonwoven fiber material layer 16 has a larger porosity on its outer side 18 than on its inner side 20. By its outer side 18, nonwoven fiber material layer 16 is arranged adjacent and potentially in abutment on the vessel wall (not shown). As achieved by the invention, tissue proliferating from the vessel wall will only partially intrude into the nonwoven fiber material layer 16. Such a proliferation of the tissue will be stopped at the latest in that region of the nonwoven fiber material layer 16 which is located on the closing body 12, particularly on the inner side 20 of layer 16 whose pore size is selected to the effect that a further proliferation of tissue through the nonwoven fiber material layer 16 will not be possible anymore.

The biostable medical nonwoven material 10 can be attached to or applied onto the outer and optionally also the inner sides 19,22 of the two optionally differently sized or also equal-sized (e.g. disk-shaped, rectangular, quadratic or generally polygonal) flanges 24, connected to each other by a central connection portion 36, of the occluder 10. The nonwoven material 15 can also be applied onto the peripheral surface of the central connection portion 26. The occluder 10 comprises a highly elastic 3D fiber mesh made of e.g. Nitinol or generally a nickel-titanium alloy, or also another elastic material which is biostable and biocompatible. The occluder 10 can be "stretched" in the extension of its central axis 28 running through its central connection portion 26 until it will assume substantially the shape of a relatively thin rod. In this state, the occluder 10 can be introduced into a catheter so as to be placed in the orifice of the cardiac septum. If, now, the biostable medical nonwoven material 15 is on the occluder 10, it will follow the elastic deformation of the fiber mesh of occluder 10, notably with advantageously little generation of folds. In this situation, the biostable medical nonwoven material 15 can be applied or have been applied thereonto either in the relaxed state of occluder 10 according to FIG. 3 or in the extended state of occluder 10. Due to its high degree of flexibility and elasticity, the medical nonwoven material 15 will "follow" the changes of the shape of occluder 10 when the latter is used prior to and during a surgical intervention.

Although the invention has been described and illustrated with reference to specific illustrative embodiments thereof, it is not intended that the invention be limited to those illustrative embodiments. Those skilled in the art will recognize that variations and modifications can be made without departing from the true scope of the invention as defined by the claims that follow. For example, in the drawings, the present invention is explained referring to a special type of a device for closing openings or cavities in a blood vessel. It is to be mentioned here that for closing openings or cavities in blood vessels also other type of devices and devices of other shapes can be used. In particular, other types of occluders which are well known in the art can be used. For example, in particular the biostable nonwoven fiber material can also be applied to an LAA occluder. In case of the LAA occluder, the nonwoven fiber material will contact the inner vessel wall of the LAA and will be exposed partially free wherein in this area of the nonwoven fiber material blood will flow so as to improve the formation of tissue as explained above.

The invention claimed is:

1. An occluder for closing openings or cavities in blood vessels or in the heart, said occluder comprising
   a closing body configured for placement over an opening or in a cavity in a wall of a blood vessel or the heart, the closing body being made of a self-expandable porous metallic fabric comprising a first flange having a first peripheral portion and a second flange having a second peripheral portion, the first flange and the second flange being connected by a central connection portion, the closing body further comprising a central axis extending through the first flange, the second flange, and the central connection portion; and,
  a first layer of biostable, nonwoven fiber material disposed on the first peripheral portion and a second layer of biostable, nonwoven fiber material disposed on the second peripheral portion that is spaced apart from said first layer of biostable, nonwoven fiber material such that said central connection portion of said closing body is exposed;
  wherein the first layer and second layer of biostable, nonwoven fiber material is composed of spray-coated fibers;
  wherein the first layer and second layer of biostable, nonwoven fiber material each has a bottom side which is in abutment on the first and second peripheral portions of the closing body, and a top side facing away from the first and second peripheral portions, and wherein the first and second layers of biostable, nonwoven fiber material on its top side comprises pores of a size different from that of the pores on its bottom side, wherein the pores on the bottom side of the first and second layers of biostable, nonwoven fiber material are smaller than the pores on the top side of the first and second layers of biostable, so that tissue proliferating from a tissue wall will only partially intrude into the first and second layers of biostable, nonwoven fiber material; and
  wherein the top side of the first and second layers of biostable, nonwoven fiber material each face in the direction of the central axis and away from the opening or cavity.

2. The occluder according to claim 1, wherein the first and second layers of biostable, nonwoven fiber material is a nonwoven random-fiber material layer.

3. The occluder according to claim 1, wherein the first and second layers of biostable, nonwoven fiber material comprises fibers having a diameter from 0.1 µm to 100 µm.

4. The occluder according to claim 1, wherein the ratio between the pore size on bottom side and the pore size on top side is 1:50.

5. The occluder according to claim 1, wherein the first and second layers of biostable, nonwoven fiber material has a thickness from 10 µm to 3000 µm.

6. The occluder according to claim 1, wherein the closing body is particularly permanently expandable, with the first and second layers of biostable, nonwoven fiber material being stretched, and wherein, prior to expansion, the thickness of the first and second layers of biostable, nonwoven fiber material is from 100 µm to 3000 µm.

7. The occluder according to claim 1, wherein the closing body is particularly permanently expandable, with the first and second layers of biostable, nonwoven fiber material being stretched, and wherein, after expansion, the thickness of the first and second layers of biostable, nonwoven fiber material is from 10 µm to 2500 µm.

8. The occluder according to claim 1, wherein the closing body is porous and particularly has a reticular structure.

9. The occluder according to claim 1, wherein the metallic fibers preferably are made of metallic memory shape alloy or Nitinol.

10. The occluder according to claim 1, wherein the first and second layers of biostable, nonwoven fiber material comprise fibers having a diameter from 0.2 µm to 20 µm.

11. The occluder according to claim 1, wherein the first and second layers of biostable, nonwoven fiber material comprise fibers having a diameter from 0.3 µm to 1 µm.

12. The occluder according to claim 1, wherein the ratio between the pore size on bottom side and the pore size on top side is 2:10.

13. The occluder according to claim 1, wherein the ratio between the pore size on bottom side and the pore size on top side is 4:8.

14. The occluder according to claim 1, wherein the closing body is particularly permanently expandable, with the first and second layers of biostable, nonwoven fiber material being stretched, and wherein, prior to expansion, the thickness of the first and second layers of biostable, nonwoven fiber material is from 150 µm to 2800 µm.

15. The occluder according to claim 1, wherein the closing body is particularly permanently expandable, with the first and second layers of biostable, nonwoven fiber material being stretched, and wherein, prior to expansion, the thickness of the first and second layers of biostable, nonwoven fiber material is between 200 µm to 2000 µm.

16. The occluder according to claim 1, wherein the closing body is particularly permanently expandable, with the first and second layers of biostable, nonwoven fiber material being stretched, and wherein, after expansion, the thickness of the first and second layers of biostable, nonwoven fiber material is from 20 µm to 2000 µm.

17. The occluder according to claim 1, wherein the closing body is particularly permanently expandable, with the first and second layers of biostable, nonwoven fiber material being stretched, and wherein, after expansion, the thickness of the first and second layers of biostable, nonwoven fiber material is between 80 µm to 1000 µm.

18. The occluder according to claim 1, wherein the closing body is configured only for placement over the opening or cavity in a wall of the heart.

19. An occluder, comprising:
  a closing body configured for placement over an opening or cavity in a wall of the heart, the closing body being made of a self-expandable porous metallic fabric comprising an outer side having a partial region arranged for blood flow therealong at least in a part of said partial region thereof when said closing body is in its state of use for closing said opening or cavity, and an inner side shaped to contact tissue;
  a central connection portion adjacent the closing body;
  wherein the radius of the central connection portion is smaller than the radius of the closing body;
  wherein the entire outer side of the closing body is coated in a layer of biostable nonwoven fiber material and the central connection portion is uncoated by the biostable nonwoven fiber material; and
  wherein the nonwoven fiber material layer is composed of spray-coated fibers, wherein the nonwoven fiber material layer has a bottom side which is in abutment on the outer side of the closing body, and a top side facing away from the outer side of the closing body, and wherein the nonwoven fiber material layer on its top side comprises pores of a size different from that of the pores on its bottom side, wherein the pores on the bottom side of the nonwoven fiber material layer are smaller than the pores on the top side of the nonwoven fiber material layer, so that tissue proliferating from a tissue wall will only partially intrude into the nonwoven fiber material layer.

\* \* \* \* \*